(12) United States Patent
Wallsten (10) Patent No.: US 7,156,860 B2
(45) Date of Patent: Jan. 2, 2007

(54) BALLOON CATHETER

(75) Inventor: Hans I. Wallsten, Denens (CH)

(73) Assignee: Wallsten Medical S.A., Denens (CH)

( * ) Notice: Subject to any disclaimer, the term of this patent is extended or adjusted under 35 U.S.C. 154(b) by 668 days.

(21) Appl. No.: 10/296,127

(22) PCT Filed: May 16, 2001

(86) PCT No.: PCT/EP01/05544

§ 371 (c)(1),
(2), (4) Date: Feb. 6, 2003

(87) PCT Pub. No.: WO01/89619

PCT Pub. Date: Nov. 29, 2001

(65) Prior Publication Data

US 2003/0149468 A1    Aug. 7, 2003

(30) Foreign Application Priority Data

May 26, 2000    (CH) ........................ 1978/00
Feb. 9, 2001    (CH) ........................ 00404/01

(51) Int. Cl.
*A61M 29/00* (2006.01)
*A61B 18/04* (2006.01)
*A61F 7/12* (2006.01)

(52) U.S. Cl. .................... 606/192; 606/27; 604/113

(58) Field of Classification Search ........... 606/27–31, 606/48–50, 192–194; 607/101–105; 604/96.01, 604/101.01, 113

See application file for complete search history.

(56) References Cited

U.S. PATENT DOCUMENTS

| 4,564,014 | A | * | 1/1986 | Fogarty et al. ............ 606/194 |
| 4,637,396 | A |   | 1/1987 | Cook |
| 4,994,072 | A |   | 2/1991 | Bhate et al. |
| 5,002,558 | A | * | 3/1991 | Klein et al. ............... 606/192 |
| 5,257,977 | A |   | 11/1993 | Eshel |
| 5,314,443 | A | * | 5/1994 | Rudnick .................... 606/192 |
| 5,330,429 | A | * | 7/1994 | Noguchi et al. ........ 604/103.12 |
| 5,423,755 | A |   | 6/1995 | Kesten et al. |
| 5,496,271 | A | * | 3/1996 | Burton et al. ............... 607/27 |
| 5,514,093 | A | * | 5/1996 | Ellis et al. ................. 604/103 |
| 5,549,551 | A | * | 8/1996 | Peacock et al. ........ 604/103.05 |
| 5,578,008 | A | * | 11/1996 | Hara ...................... 604/96.01 |
| 6,884,257 | B1 | * | 4/2005 | Cox ......................... 623/1.11 |

FOREIGN PATENT DOCUMENTS

DE    39 05 827    9/1989

(Continued)

*Primary Examiner*—Michael Peffley
(74) *Attorney, Agent, or Firm*—Buchanan, Ingersoll & Rooney PC (57) ABSTRACT

The invention relates to balloon catheters (1) and methods of treatment for exerting internal pressure on surrounding tissue of a mammalian duct or cavity in a section thereof having a substantially circular cylindrical configuration. The elongate rigid distal section and the intermediate section of the catheter contain a central tube (3), whose distal part is provided with at least one outlet (23) for medium within the balloon, and whose intermediate part is surrounded by an axially displaceable tube (4), onto whose distal end the proximal end of the balloon is attached. The balloon has an envelope which is constituted by at least one substantially gas- and liquid-impermeable and elastic internal layer and an external layer of limited radial expansion, said expansion being substantially independent of the axial length of said balloon. The balloon may he encompassed by a radially expandible stent (40), or can be equipped with means for supplementing treatment using pressure with heat treatment.

44 Claims, 3 Drawing Sheets

FOREIGN PATENT DOCUMENTS

| | | |
|---|---|---|
| EP | 0 678 307 | 10/1995 |
| EP | 0 923 912 | 6/1999 |
| FR | 2 657 773 | 8/1991 |
| GB | 1566674 | 5/1980 |
| WO | WO 92/11824 | 7/1992 |
| WO | WO 96/40345 | 12/1996 |
| WO | WO 97/28840 | 8/1997 |
| WO | WO 99/07315 | 2/1999 |
| WO | WO 99/08634 | 2/1999 |
| WO | WO 00/35391 | 6/2000 |

\* cited by examiner

BALLOON CATHETER

FIELD OF THE INVENTION

The present invention relates to devices and methods for the treatment of mammalian tissues using pressure or pressure combined with heat. Examples of such mammalian tissues including human-tissues are found in arteries, prostate and oesophagus.

BACKGROUND ART

Catheters using an extensible balloon have many areas of use in medical technologies. It is often related to the treatment of restrictions in certain organs which are accessible only via narrow passages. With the balloon in a deflated state it is introduced into the site of treatment and is then made subject to expansion. For certain purposes balloons having a limited elasticity in a radial direction are used i.e. the balloon takes a predetermined shape when distended, for example cylindrical shape.

Such balloon catheters have been extensively used to open restrictions, so called stenoses, in for example the vascular system. This treatment, so called PTC- or PTCA-techniques, take place under several bars of pressure, and it is therefore important that the balloon can expand only up to the predetermined diameter so as to avoid damage to the vessel by over-dilation.

For the treatment of benign prostate enlargements (BPH) it has been suggested to dilate urethra and prostate using a balloon of restricted radial expansion which, when distended from a dilated diameter of about 5 to 7 mm forms a cylinder having a diameter of about 30 mm. The inflation of the balloon must take place under high pressure in view of the resistance of the surrounding tissue.

As a material for dilation balloons for PTA, PTCA or dilation of the prostate different flexible but inelastic materials are used. One example is polyethylene terephtale (PET). This material can be pre-shaped and has high mechanical strength in spite of a wall thickness of only 0.03 to 0.04 mm which is an advantage, in particular in relation to dilation of fine blood vessels.

A drawback of such inelastic material is, however, that folds are formed when the balloon is in an unexpanded state, for example when the balloon catheter is introduced into or withdrawn from fine bodily ducts. In U.S. Pat. No. 5,423,755 (Kesten et al.) there is described a balloon catheter for dilation of urethra and prostate, the balloon being made of such inelastic material. In order to reduce the formation of folds both ends of the dilation balloon are each attached to two telescopically arranged central tubes. A spring has bias separate the two tubes axially so that the balloon is maintained in a stretched position when the system is unpressurised. When pressure is supplied the balloon diameter increases at the same time as the balloon length will be reduced in view of the acting forces until the predetermined balloon dimension in regard to diameter and length has been reached. In this manner the formation of folds across the balloon will be reduced but the problem of axial folding remains.

In the patent No GB 1566 674 (Hanecka et al.) there is described a similar balloon catheter for dilation of blood vessels, oesophagus, ductus scholedochus, the formation of folds being reduced by the use of two co-axial tubes, one slidable, within the other to prevent an irregular and unlimited extension. The balloon is reinforced by a synthetic fabric embedded in the balloon. The filaments of the fabric extend along helices of opposite sense so that only a limited extension in the radial direction is allowed. For introduction the balloon is stretched in an axial direction increasing its length by 60% and simultaneously decreasing the diameter to 40% of the pressurised balloon. At pressurising the balloon will expand in a radial direction to the desired diameter while its length becomes shortened. In case of stenoses which are longer than the balloon the catheter is inserted further and the expansion repeated.

In U.S. Pat. No. 5,314,443 (Rudnick) there is described a similar balloon catheter with two co-axial slidable tubes where the elastic balloon material is constituted by for example polyurethane, silicone or latex reinforced with glass fibre, nylon or carbon fibres, which are materials of low elasticity.

In U.S. Pat. No. 4,637,396 (Cook) there is described a balloon catheter using an elastic balloon for dilation to a certain predetermined diameter. The balloon wall consists of three layers, one inner elastic tight urethane membrane, a middle layer of a knitted fabric tube and an outer layer of an elastic impervious urethane membrane. The three materials are attached together at their ends and form a tube-shaped balloon.

The material of the knitted fabric tube is a yarn of limited elasticity, for example composed of inelastic strong fibres, such as Dacron, and by elastic fibres, for, example Spandex. When such yarn is stretched it is extended by its elasticity up to a certain limit at which the inelastic fibres of the material are fully stretched and can absorb relatively strong forces.

The advantage of this balloon catheter is that there is a minimum of fold formation and that there is no change of length when the balloon is inflated or when the pressure is released. Accordingly, this results in a simple design with the balloon attached to one single central tube. In this manner a balloon is obtained which has the same fixed length both as deflated and inflated.

When treating certain human organs it is important that the dilatation takes place only at a precise predetermined site and for a length which is adapted to the restriction to be treated. As an example there can be mentioned dilatation of an enlarged prostate at BPH. In dilatation using for example ASI UROPLASTI™ Dilatation system, Advanced surgical intervention Inc. USA, it is important that the proximal end of the balloon is positioned at the apex adjacent to the external sphincter and that it should not extend beyond the bladder neck. Since the length of the prostate varies to a large extent from patient to patient this length must first be determined using a special calibration catheter with a Foley balloon in the distal end under cystoscopy after which the urologist selects the correct balloon size. Therefore, nine catheters with balloon lengths in a range between 15 to 55 mm must be available with 5 mm increments. To allow exact positioning of the selected balloon catheter this has a separately expandable Folley balloon at the distal end of the catheter for precise placement of the distal end of the dilatation balloon at the bladder neck.

In certain cases restrictions are treated with a combination of pressures and heat from a heat-releasing balloon. U.S. Pat. No. 5,257,977 (Eshel) thus describes a method for the treatment of enlarged prostate with an expandable balloon. A heater fluid supply inflates under a pressure of 1–4 atm a balloon and provides a pressure and heat treatment to the prostate and bladder neck. The corresponding catheters commercially available from Argomed Inc, Morrisville, USA. Even in this case catheters in 9 different balloon lengths from 2 to 6 cm are available. This is, of course, a significant disadvantage and involves high costs for manufacture and storage both for producer and hospital.

OBJECTS AND SUMMARY OF THE INVENTION

The main object of the present invention is to provide a balloon catheter for the treatment of a mammalian, including human, duct or cavity by exerting internal pressure on a surrounding tissue, the catheter being provided with a balloon the expansion of which is substantially independent of the axial length of the balloon.

Another object of the invention is to provide a method for the treatment of such duct or cavity in a section thereof having a substantially circular cylindrical configuration, internal pressure being exerted on the surrounding tissue of said duct or cavity.

Yet another object of the invention is to provide a balloon catheter provided with a balloon the axial extension of which can be varied to match treatment sites of different lengths.

A further object of the invention is to provide a balloon catheter and a method associated therewith which is provided with a positioning balloon attached at the front end of the catheter for correct positioning of the catheter before treatment.

Still another object of the invention is to provide a balloon catheter and a method where the balloon carries a radially expansible stent capable of synchronous expansion with a balloon, said stent being left behind in the site of treatment after withdrawal of the catheter.

Another object of the invention is to provide a balloon catheter and a associated method wherein the treatment of pressures exertion is combined with heating.

Accordingly, a first aspect of the invention is the provision of a balloon catheter for exerting internal pressure on surrounding tissue of a mammalian duct or cavity in a section thereof having a substantially circular cylindrical configuration. Said balloon catheter comprises a elongate rigid distal section and a flexible and elastic balloon accommodating said distal section, further-comprising means for the supply of a pressure medium for the expansion of the balloon. The catheter further comprises an intermediate section and a proximal section for operating the device. Said latter section can for convenience be flexible.

As characterising features for this balloon catheter said and intermediate sections contain a central tube, whose distal part is provided with at least one outlet for said medium within the balloon, and whose intermediate part is surrounded by an axially displaceable tube, onto whose distal end the proximal end of the balloon is attached. Furthermore, said balloon has an envelope which is constituted by at least one substantially gas- and liquid-impermeable and elastic internal layer and an external layer of limited radial expansion, said expansion being substantially independent of the axial length of the balloon.

According to a second aspect of the invention there is provided a method for the treatment of a mammalian duct or cavity, said method comprising the steps:

a) estimating the axial extension of said section;

b) adjusting and securing the distance between the axial ends of an elastic balloon to match said axial extension;

c) inserting the balloon thus prepared into said duct or cavity section;

d) expanding said balloon by introducing a pressurized fluid therein to exert pressure on said walls to widen to a predetermined degree said duct or cavity within said section by using a balloon of predetermined limited radial expansion;

e) deflating said balloon and-withdrawing same from said duct or cavity section.

In regard to the two-step procedure it can be noted that the second step of renewed insertion for implantation of a stent makes use of the balloon length calibration made in the first step.

According to a third aspect of the invention there is provided a balloon catheter for exerting internal pressures on surrounding tissue of a mammalian, including human, duct or cavity in a section thereof having a substantially circular cylindrical configuration. This balloon catheter comprises an elongate rigid distal section and a flexible and elastic balloon accommodating said distal section which, together with said balloon is intended for insertion into said duct or cavity section, further comprising a central tube contained in said distal section and whose distal part is provided with at least one outlet for said medium within said balloon. Characterizing features of this balloon catheter include that the balloon has an envelope which is constituted, by at least one substantially gas- and liquid-impermeable and elastic internal layer and an external layer of limited radial expansion, and further a radially expansible stent encompassing said balloon, said stent being deformable to expand synchronously with the radial expansion of the balloon when inserted in said duct or cavity, thereby being retained expanded therein upon withdrawal of the catheter from said duct or cavity, means generating circulation of said medium within or through said balloon, and heating means for combining pressure treatment with heat.

A fourth aspect of the invention resides in a method of treatment of mammalian tissue of a mammalian duct or cavity in a section thereof having a substantially circular cylindrical configuration, said method comprising the steps:

a) applying onto a balloon before insertion thereof a radially expansible stent capable of radial deformation;

b) inserting the balloon thus prepared into said duct or cavity section;

c) distending said balloon by introducing a pressurized fluid therein to exert pressure on said tissue to widen to a predetermined degree said duct or cavity within said section and to expand the stent by using a balloon of predetermined limited radial expansion; and e) removing fluid from said balloon and withdrawing same in a collapsed state from said duct or cavity section leaving the stent behind in an expanded state.

As an alternative to this aspect of the invention there is provided a method comprising the steps:

a) estimating the axial extension of said section;

b) adjusting and securing the distance between the axial ends of an elastic balloon to match said axial extension;

c) applying onto a balloon before insertion thereof a radially expansible stent;

d) inserting said balloon carrying said into said sections;

e) expanding said balloon by introducing a pressurized fluid to expand the stent; and f) releasing the pressure to deflate the balloon and withdrawing same while leaving the stent behind in an expanded state.

Common to all embodiments involving a stent carried by the balloon is the feature of axial adjustment of the stent in length to conform to the balloon of likewise adjustable axial extension.

It goes without saying that the stent can be adapted in length by cutting it in advance to the desired length.

In this disclosure the expressions "distal" and "proximal" are used with the meaning "front" and "rear", respectively, i.e. related to the operator of the instrument or device.

DETAILED DESCRIPTION OF THE DRAWING

The invention will in the following be further described by exemplifying embodiments which, however, must not be construed to restrict the scope of protection except as defined in the appended claims. These embodiments are described with reference to the appended drawings, wherein

DESRIPTION OF THE PREFERRED EMBODIMENTS

Figure 1:
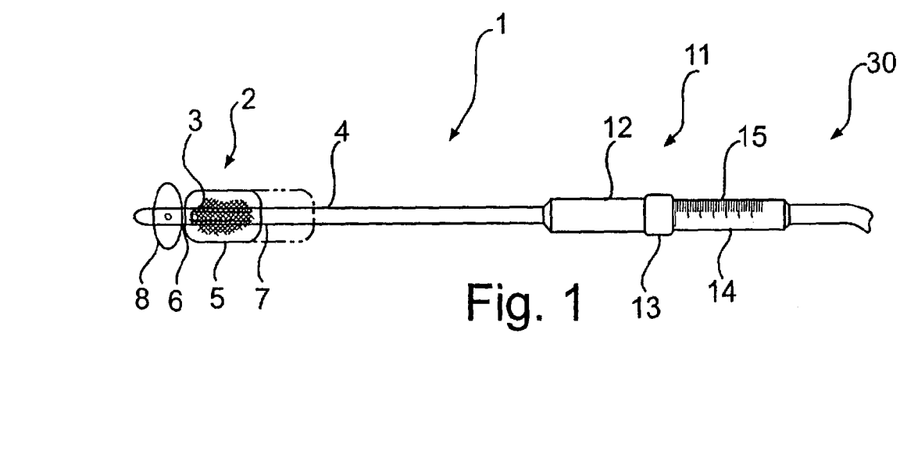
FIG. 1 is a simplified diagrammatic illustration of a device according to the present invention.

FIG. 1 shows diagrammatically in a side view an embodiment of the invention in the form of a catheter generally designated 1 for the treatment of benign prostate hyperplasia (BPH) using pressure and heat. This results in an efficient combination of widening of the prostate and partial necrosis of prostate tissue. As seen to the left in FIG. 1 there is shown the distal end 2 of the catheter intended for insertion from the outside through the urethra and which comprises two concentric tubes 3, 4 which are axially displaceable relative each other, tube 4 partly enclosing tube 3. An elastic, inflatable balloon 5 for the treatment with pressure and heat is at its distal end attached to tube 3 at 6 and at its proximal end attached to tube 4 at 7. The balloon 5 is in possession of special properties to be described below so that it in an inflated position takes an elongate shape with predetermined diameter and length as illustrated by the full lines. At the outermost distal end of catheter 1 a second, inflatable balloon 8 is arranged for positioning of the catheter during treatment so that the active part of balloon 5 will be correctly positioned between bladder neck and the external sphincter.

Catheter 1 also includes an intermediate section 11 containing an enlargement 12 of tube 4 and a locking nut 13 together forming a handle. The enlargement 12 and the locking nut 13 surround the body 14 which is interiorally connected to tube 3. Accordingly, the length of the elastic balloon 5 can be varied by displacement of the handle. The length of the balloon can be read on a scale 15 on body 14 and the desired length can be maintained by turning the locking nut 13.

Catheter 1 has a proximal part 30 shown significantly shortened and comprising a flexible tube for connection to a control unit (not shown) and conduits for the supply of medium for the expansion of balloons 5 and 8 and for the circulation of heating medium from an external heat source through balloon 5.

Figure 2:
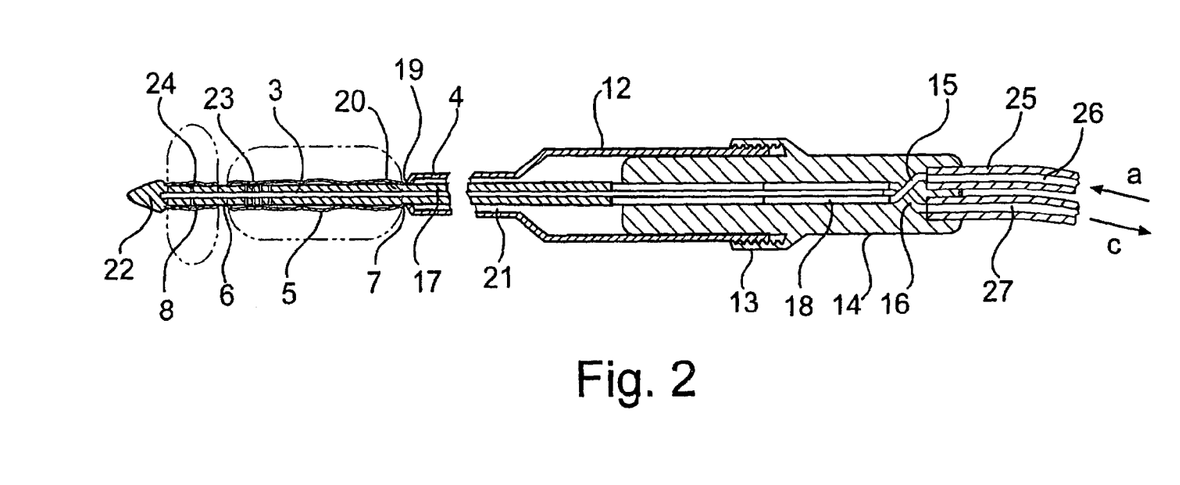
FIG. 2 is a more detailed diagrammatic illustration, partly in section, of the device shown in FIG. 1.

FIG. 2 shows more in detail a section through the apparatus of FIG. 1. The different parts have been given the same reference numerals in both figures. Balloons 5 and 8 are in FIG. 2 shown by full lines in deflated condition and by dashed lines in expanded position.

The body 14 contains passages 15 and 16 connected to a flexible multilumen tube 25 containing an inlet lumen 26 and an outlet lumen 27 for the introduction of a heating medium and discharge of the medium, respectively (arrows a and c). Concentric to the tube 3 and the axially displaceable tube 4 there is arranged an intermediate tube 17 extending from the distal end of tube 4 and proximally into a bore 18 provided in the body 14. At the distal end thereof the intermediate tube 17 is sealingly attached to an inward flange 19 on the tube 4. In this manner tubes 4 and 17 can be axially displaced as a unit for the adaptation of the balloon length as described above. By the concentric arrangement of the intermediate tube 17 around tube 3 there is provided an outlet passage gap 20 opening providing connection inside the body 14 with the outlet passage 16. Between the intermediate tube 17 and the surrounding axially displaceable tube 4 an insulating annular space 21 is formed acting as a heat insulation to prevent excessive heating of the urethra.

Openings 23 in tube 3 provide connection between the inlet lumen 26, the passage 15, the interior of the tube 3 and the interior of the balloon 5. In the distal section of the tube 3 sleeve 22 is arranged concentric with the tube 3. Openings 24 provide connection with a fine tube (not shown) positioned in the inlet lumen 26, along the passage 15, the tube 3 and the interior of the balloon 8.

As mentioned tube 25 is intended for connection to a control unit (not shown) from which a heat-carrying medium, for example a liquid, can be introduced into the catheter. During treatment the medium is heated in an externally arranged heat exchanger to the desired temperature and is circulated by means of an external pump in a circuit comprising pump, heat exchanger, control unit for inter alia control of pressure, temperature, amount of liquid, etc.

Figure 3:
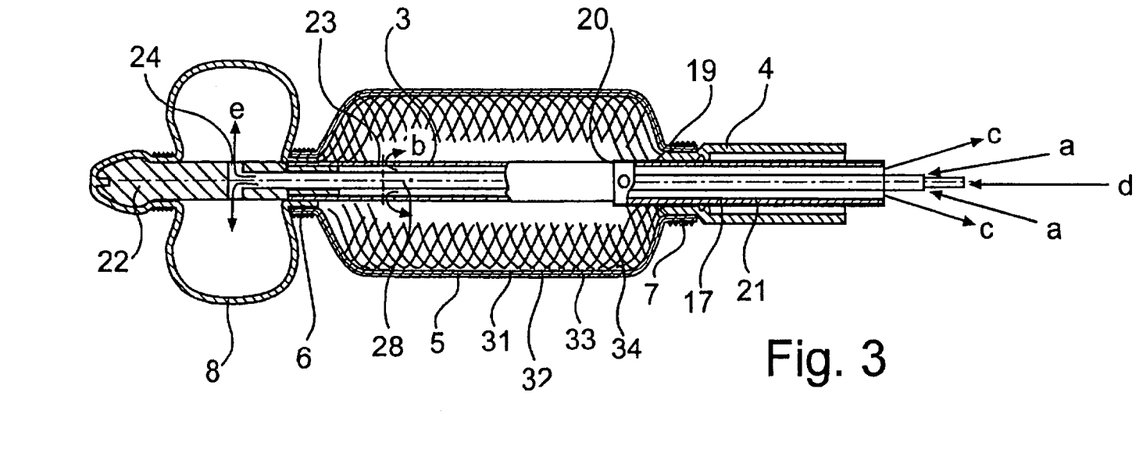
FIG. 3 is a side view, partly in section, of a specific embodiment of the device according to the invention.

FIG. 3 shows a detail of the distal part 2 of the catheter. In FIG. 3 the same reference numerals have been used as in FIGS. 1 and 2. Arrows a and b show supply of heating medium and arrow c the discharge thereof. The fine tube mentioned earlier extending in tube 3 has, been designated 28 and is connected with an aperture 24 in the sleeve 22 for supply of a medium, for example air, for the distension of the balloon 8 for positioning of the catheter in the urethra (arrows d and e).

Figure 4:
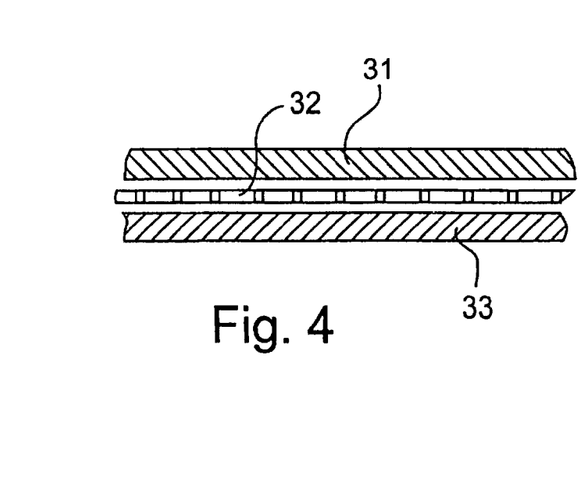
FIG. 4 shows diagrammatically an enlarged detail in section of the balloon enclosure.

Balloon 5 is shown in its expanded state. The enclosure of the balloon consists of three layers—one inner layer 31, one intermediate layer 32 and one outer layer 33 as shown in detail in FIG. 4. Layers 31 and 33 consist of a thin, liquid-tight highly elastic film of an elastic material, such as silicon film. The intermediate layer 33 is constituted by a braid of a yarn with limited elasticity. The yarn has a core of elastic polyurethane, for example Lycra®, around which filaments of inelastic fibre, such as nylon, have been spun. The yarn is quite stretchable and can be stretched out to a certain maximum limit until the inelastic filaments are fully extended. In the stretching the diameter of the yarn decreases. Suitable stretchability is in this case about 350%. By this percentage is meant that the stretch is 350% greater than the original length of the yarn. With the balloon in an expanded state the threads of the braid have been stretched to the maximum limit and the threads or filaments form a network of 64 crossing filaments determining the shape of the balloon.

Figure 5:
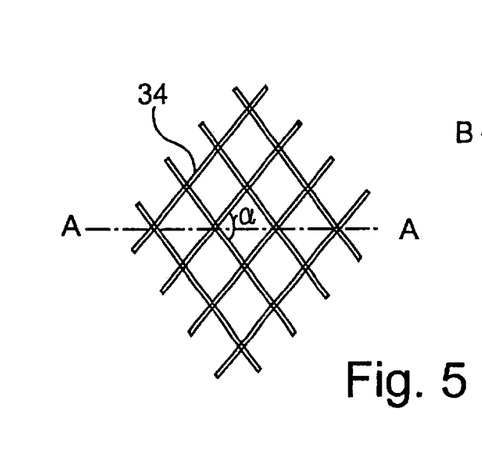
FIG. 5 is an enlarged detail of the braid of the intermediate layer of the balloon.

FIG. 5 shows a detail of the network where the longitudinal axis of the balloon has been indicated with A—A and the angle between the crossing filaments as seen in the direction of the longitudinal axis has been designated α.

It has now been surprisingly found that by using the device according to FIGS. 1 to 3 it is possible to adjust and set different balloon length by axial displacement of tube 4 relative to tube 3, the highly elastic three-layered balloon material being stretched in a corresponding degree without affecting the diameter of the balloon in a distended state. This is important from a medicinal viewpoint since it allows for treatment of prostates of different lengths but under otherwise similar conditions. The invention also makes it possible to perform exact setting of the balloon length and by suitable selection of properties of the material of the balloon it is possible with one and the same catheter to double a certain given minimum balloon length while maintaining the same diameter in expanded state. In this manner it is possible to cover a span of prostate lengths of from about 20 to about 60 mm using only two catheters, one of which covers the range 20–35 mm and the other 35–60 mm. Each catheter can be adjusted with an accuracy of one millimetre. This can be compared with previously mentioned catheters from Advanced Surgical Intervention and Argomed Inc. requiring manufacture and storage of 9 different catheters each of fixed balloon length.

The procedure in the treatment of BPH will be as follows. First, the operator determines in a manner known per se using a cystoscope the length of the prostate between the bladder and the apex. Then, the adequate instrument with regard to length range and diameter in expanded condition is selected and the predetermined length is set by displacement of tube 12. Then, the setting is fixed using locking nut 13.

The catheter connected to the external system is filled with liquid, for example glycine; is inserted via the urethra to a position where balloon 8 is positioned inside the bladder neck. The balloon 8 is then distended by the supply of a suitable quantity of air (for example 15 ml). The catheter 1 is somewhat retracted so that balloon 8 rests against the bladder neck and is maintained in this position during the whole treatment procedure.

Alternatively, the adjustment of the balloon length can take place after insertion of the catheter by positioning the proximal attachment 7 of balloon 5 in relation to the apex. This can be done using a cystoscope or fluoroscope.

Balloon 5 is then distended by the supply of further amount of liquid to the system, suitably to an overpressure of about 0.5–2 bar, which normally is sufficient to give even a very uneven urethra a cylindric shape conforming to the distended balloon.

The treatment can now start by the circulation of the heat-emitting medium as described so that an adequate treatment temperature can be maintained during the treatment period. As an example there can be mentioned a treatment temperature of about 55 to 90° C. for about 10–60 minutes.

The system for external heating and circulation as described with reference to FIGS. 1 to 3 can advantageously be replaced with the system which is described in PCT-application SE99/02396 "Device and method for medical treatment" in connection to FIGS. 4, 5 and 6. The disclosure of this patent application is incorporated herein by reference.

As mentioned earlier the balloon described in relation to FIGS. 1 to 3 consists of three separate layers one inner layer and one outer layer consisting for example of a liquid-tight silicon film, and an intermediate layer of a braid of a yarn of limited elasticity.

For the inner and outer layers it is advantageous to use a material which is highly elastic and capable of substantial elastic elongation as well as radial extension. It is preferred that the material has an elongation to break of at least more than about 700% and preferably 100% or more. A silicon rubber, such as a material manufactured and sold by Dow Corning is suitable and if axially extended up to say three times it can still be radially extended four to five times.

In the described embodiment the three layers are free in relation to each other when the balloon is deflated except for the two ends thereof where they together are liquid-tight fixed to tube 3 and the flange 19 (FIG. 3) by a suture winding.

As previously mentioned it is the elasticity properties of the yarn and the braid configuration which will, determine the shape of the inflated balloon, it is desirable that the stretchability of the braid axially is maintained and it is therefore suitable to fix same unstretched when assembled. In order that the balloon in an expanded state shall take a stable shape symmetrically surrounding the central tube 3 and tube 4 it has been found suitable in the assembly thereof to pre-stretch at least one of the two silicon layers 31 and 33 (FIG. 4) or, alternatively, to stretch all three layers 31, 32 and 33 by an extension of about 50–100%. As an example there can be mentioned a catheter manufactured for pressure and heat treatment of BPH having the following specifications.

A braid is manufactured of 64 crossing yarns of restricted elasticity consisting of a core of Lycra® spun around by a nylon thread. The yarn has a d-tex value of 80 and a stretchability of 350%. The braid in the form of a stocking of about 4 mm diameter is passed onto a tube of highly elastic silicon (Dow Corning) stretched by 50%. The wall thickness of the tube is 0.2 mm and its diameter 5 mm. An outer silicon tube of the same dimensions is applied without pre-stretching, whereafter the three-layered balloon is attached to two concentric tubes corresponding to tubes 3 and 19 as earlier described: The attachment is at 6 and 7 (FIGS. 2 and 3) suitably by using a suture winding.

The distance between the two sutures, i.e. the shortest balloon length is 15 mm. In assembly the balloon is stretched so that the shortest balloon length is 20 mm. In an unexpanded state the balloon has a diameter of 5 mm, which is suitable for insertion into the urethra. The balloon is applied to the catheter and distended by liquid to a pressure of 1 bar. The diameter is measured to 22 mm. The angle α (FIG. 5) between the crossing threads is about 120°. The liquid is then evacuated, and different balloon lengths from 20 mm up to 40 mm can be adjusted and the balloon expanded to 1 bar. The variations in diameter in these measurements is only 1 mm, i.e. ±5. The same result is obtained at a pressure of 1.5 bar.

It has been found in relation to the described embodiment of the balloons consisting of three separate layers that there is a risk that the threads of the balloon can slide sidewise at high pressures, which can result in an uneven balloon shape. This can be prevented by having the intermediate layer 32 of limited elasticity (FIG. 4) incorporated in or attached to the surface layer of one of the outer layers 31 and 33. This can be done in connection with extrusion or injection moulding of the film layer. In another embodiment the intermediate layer 32 is attached to at least one of the outer layers 31 and 33 using an elastic adhesive. Alternatively, the intermediate layer is imbedded in one single layer of silicon.

In view of the fact that the intermediate layer 32 is incorporated in or attached to the surface of at least one of silicon layers 31 and 32 sliding sidewise is prevented, and it has been found that balloons of this type can withstand very high pressures, for example 3–5 bar or more.

Thin films of silicon have a relatively high gas penetration. It has been found that air is often released and assembles in-balloons using a liquid as a expansion medium. In the embodiment describe with three different layers air can penetrate through the inner silicon layer in view of the gas penetration capacity thereof and remain between the two silicon layers and even separate the layers impairing the heat conduction through the layers.

This can be prevented by first attaching the inner layer 33 and the intermediate layer 32 of the balloon liquid-tight to tubes 3 and 4 by for example a winding of sutures, the outer layer being then applied onto the intermediate layer 32 with or without adhesive-attachment. In this manner gas, for example air, collected in the balloon can leak out into the intermediate layer in view of the overpressure and vanish out between the suture winding and the surrounding outer layer.

Figure 6:
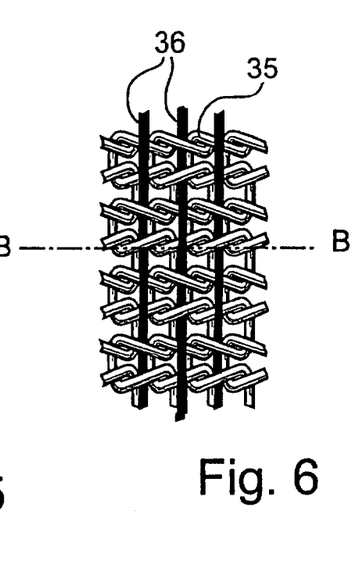
FIG. 6 shows a detail of an alternative arrangement of the intermediate layer of the balloon.

In the embodiments hitherto described the intermediate layer consists of braids of yarn of limited elasticity which in most cases are preferred. However, such braids can be replaced with a knitted fabric, for example consisting of a series of spaced loops made of one single yarn of limited elasticity. It has been found suitable that such knitted structure contains an extra interwoven filament of limited elasticity in a spiral configuration. FIG. 6 illustrates such an embodiment, wherein B—B designates the longitudinal axis of the balloon, 35 the knitted structure and 36 the interwoven filament. In such embodiment the elastic structure 35 functions as a support for the spiral 36 restricting the radial expansion at the same time as movability in an axial direction is possible without substantially affecting the radial expansion capacity according to the inventive concept.

In the embodiment according to FIGS. 1–3 the positioning of the treatment balloon 5 relative to the prostate to be treated takes place by using the separate inflatable positioning balloon 8 which during treatment is maintained in position against the bladder neck as described above.

Alternatively, the balloon 8 can be connected to the system for the supply and circulation of the pressure-heating medium. In this case the fine tube 28 can be eliminated and openings 24 of tube 3 can open in balloon 8 instead of in balloon 5. If connection passages between balloons 8 and 5 are arranged between tube 3 and the attachment at 6 (FIG. 3) the heating medium can be circulated first through balloon 8 and then through balloon 5. Balloon 8 can in this case act as a positioning balloon and also for heat treatment of the bladder neck.

It is known since long to heat treat BPH using high frequency heating, such as microwave heating. This takes place with catheters in the distal part of which a microwave antenna is encapsulated. The antenna transmits microwaves creating heat into the prostate. The frequencies used are between 900 and 1300, MHz. Correct positioning of the antenna is achieved with a positioning balloon at the tip of the catheter. To match the length of the prostate catheters with different antenna lengths are available. The antenna is surrounded by a tube with canals wherein a stream of cold water protects the urethra from the heat induced by the microwave cabling. A disadvantage of this method is that it does not enable simultaneous treatment with heat and pressure.

In another embodiment of the invention this is made possible by using a heat source constituted by a microwave antenna or radio-frequency emitter centrally positioned in the balloon, whereas the medium for the expansion of the balloon is a pressurised circulating cooling medium. In this manner there is obtained an improved effect of the generated heat by the fact that the prostate tissue is compressed at the same time as the urethra is protected from the heat.

It is known in less invasive systems for the treatment of BPH in the form of thermotherapy with e.g. laser or microwave, there is a swelling of the prostate, which increases retention and decreases the flow rates of urine due to this obstruction. This calls for a long catheterisation time compared to the present predominant treatment resection TURP, which is a drawback.

It has therefore been suggested to insert a stent after the thermotherapy. Different types of metallic stents are available for the treatment of stenoses. A drawback is that such devices need a special catheter for insertion and expansion. An example is a balloon catheter with the unexpanded stent fixed around the deflated balloon at the tip of the catheter. After insertion the balloon is inflated so that the stent expands to a predetermined diameter. For the treatment of for example BPH a non-degradable stent is preferably removed after some time.

As an alternative it has been suggested to use biodegradable stents, which completely degrade after the therapy. Suitable materials for such stents are for example polymers of poly-K-hydroxiacids such as polyglycotic acid (PGA) or polylactic acid (PLLA) used since many years in bone surgery. These materials are thermoplastic and can be thermoformed or drawn in the form of strips or wires and formed to for instance spirals.

An example of such a spiral for the treatment of BPH is the spiroflo® stent (Mentor, USA) which is made of a copolymer of PGA and PLLA (PLGA). This spiral can be inserted with the help of a cystoscope. Although such stents can self-extend somewhat after insertion due to influence of the body temperature, the extension is moderate.

For the use after treatment with pressure and heat it would be desirable with high radial expansion rates of 3 to 5 times of the stent to get a good fixation.

It has now been found possible to use catheters within the inventive concept for the treatment of for example BPH using pressure and heat; for a subsequent implantation of a stent of a thermoplastic, viscoelastic degradable material, such as polyglycolide (PGA):, poly-l-lactide (PLLA), poly-L-D-lactide (PLA) or a copolymer of polylactide and glycolide (PLGA). The implantation can take place immediately after conclusion of the heat/pressure treatment and removal of the balloon catheter. The stent is passed on-to the deflated balloon and the catheter is then reinserted and the balloon once more distended. The stent expands in harmony with the expansion of the balloon in view of its elasticity and simultaneous mechanical deformation.

The balloon is expanded to a suitable diameter, and when the expansion is finished the expanded stent is fixed between the wall of the urethra and the balloon. Heated liquid is then circulated though the balloon at a suitable temperature adapted-to the softening temperature of the stent material (or its glass transition temperature), for example 60–90° C., and the heat treatment is then concluded. After cooling the stent will thus maintain its expanded state. In this manner obstruction in view of the swelling during the healing period will be prevented. Alternatively, the expansion of the stent can be facilitated by initiating heating when the catheter has been positioned at the same time as the expansion is started.

The expansion of the stent can also take place through the viscoelastic memory properties of the material. Thus, the stent can be constituted by a spiral produced from a filament of e.g. PLGA drawn with straight, configuration or wound to a spiral with a large diameter at a temperature near melting but which then in a cold condition has been wound to a spiral of small diameter, for example 5 mm.

It has been found that such spiral mounted onto a balloon catheter according to the invention expands by itself when heated to a diameter depending on the temperature so that the diameter will be larger the higher the temperature. In this manner for example spiral stents with a minimum diameter of 5 mm can be produced which expand to for example 12 mm diameter at a temperature of about 50° C. In other words, it is possible to determine the diameter of the expanded stent by selection of temperature.

The method described above of implanting a stent using the treatment catheter has many advantages. Thus, it involves cost saving in view of the fact that no special introduction instrument will be needed. At the same time the stent will be placed in correct position in the urethra and will expand quickly so as to obtain good fixation. It has also been found possible to use catheters according to the invention for treatment of for example BPH with pressure and heat with simultaneous implantation of a degradable stent of a thermoplastic viscoelastic degradable material as previously described. In this case the procedure will be as follows.

After establishing the length of the treatment site and adjusting the balloon catheter correspondingly a stent of corresponding length is mounted onto the balloon. Before insertion the pressure will be somewhat increased so that the stent will be kept in position but without expansion. When the catheter has reached the correct position balloon and stent are expanded during heating to the diameter required for adequate treatment at the same time as the material of the stent will soften. After finished treatment heating is interrupted and the stent will rigidify and maintain the diameter taken by the balloon after interrupted heating. By partial deflation of the balloon adaptation of the stent diameter can be made by measuring the volume of discharged pressure medium.

In for example treatment of BPH a suitable balloon diameter can be for example about 20 to 25 mm. However, it is desirable that the diameter of the stent after cooling is only about 12 to 14 mm. It has been found possible to produce a stent of for example PLGA which can be expanded to a large diameter during heat treatment, and the stent can then take a smaller diameter during the healing period by making use of the memory properties of the material.

Thus for example a spiral stent can be manufactured from a monofilament wound to a spiral configuration with for example a diameter of about 12 mm at a temperature near melting temperature. The stent is then shaped in a cold condition to a spiral of a small diameter, for example 6 mm. Such stent will when heated tend to expand to an extent which is dependent on temperature. It has been surprisingly found that if such stent having a diameter of 6 mm is mounted onto a balloon catheter according to the invention and introduced into the urethra for the treatment of BPH it can expand to the desired diameter, for example 22 mm, under the influence of heat and pressure. When the treatment is concluded and the balloon is deflated the stent will take a reduced diameter and the desired final diameter can be obtained by adaptation of the diameter it was given during the original preparation of the stent.

According to one embodiment of the invention the stent will be assembled with the catheter so that it surrounds the balloon already in manufacture. One requisite is that the stent is stretchable in an axial direction. By having such stent attached to the balloon at least at both ends thereof the stent accompanies the balloon when the balloon length is adjusted. In this manner the measures taken by the operator will be substantially facilitated and exact positioning of the stent will be obtained.

Figure 7:
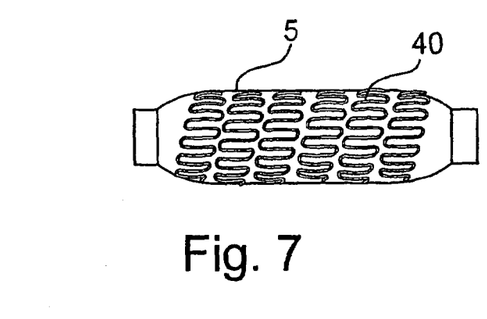
FIG. 7 is a detail of the balloon carrying an expandable stent.

A number of stent configurations are conceivable for this purpose. In FIG. 7 there is shown a stent generally having a spiral configuration but extended in zigzag in the cylinder plane of the spiral. Expansion is possible radially in view of the straightening of the zigzag shape at the same time as the stent is axially stretchable in view of its spiral shape.

Figure 8:
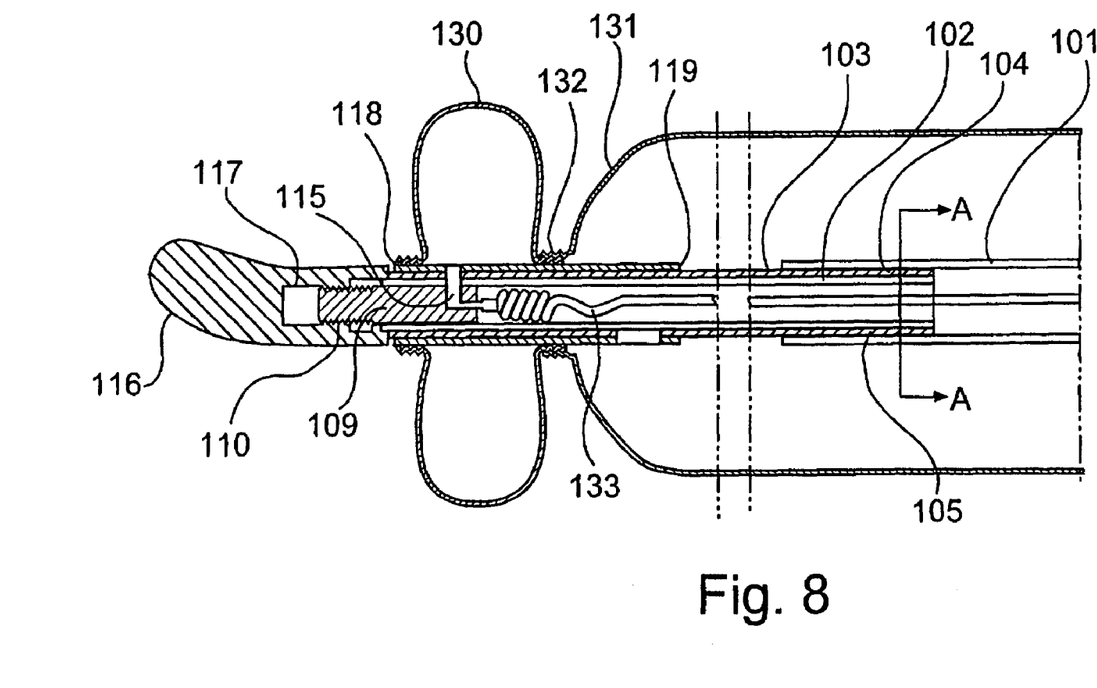
FIG. 8 is a simplified illustration of the distal end of a balloon catheter according to the invention enabling an alternative arrangement for adjusting the axial extension of the balloon.
Figure 9:
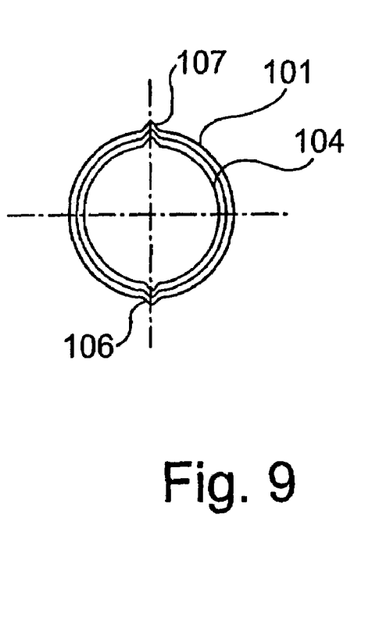
FIG. 9 shows an enlarged view in section a detail a seen along line A—A in FIG. 8.

FIGS. 8 and 9 show an alternative arrangement for adjusting the axial length of the balloon to match treatment sites of different sizes. The device shown in FIG. 8, illustrating the distal part of the balloon catheter only, contains two telescopically arranged tubes a central tube 101 and a telescopic tube 102 within the central tube 101 and an intermediate tube 103. All tubes fit tightly within each other and are axially displaceable relative to each other. A stop ring 104 is attached onto and at the proximal end of the telescopic tube 102 and is constituted by a short tube having the same size as the intermediate tube 103. Between tube 103 and the stop ring 104 a locking ring 105 of an elastic material is arranged. The central tube 101 has two extensions 106 and 107 extending axially. In a corresponding manner there are two extensions in stop ring 104 which have for an effect that the telescopic tube 102 having the stop ring 104 and the intermediate tube 103 can be axially displaced in central tube 101 but not rotated. If on the other hand the intermediate tube 103 is axially displaced in relation to the telescopic tube 102 and the stop ring 104 so that the elastic ring 105 will be expanded, then the telescopic tube 102 will be locked in relation to the central tube 101.

In the distal part of the telescopic tube 102 an elongate body 109 has been firmly inserted. Body 109 is provided with an exterior thread 110 and contains a canal or passage 115.

The distal part 116 of the catheter can be permanently bent upwardly and contains a bore 117 having an interior thread co-operating with thread 110 in body 109.

A sleeve 118 is attached to and surrounds the distal part of intermediate tube 103. The proximal part 119 of this sleeve 118 acts as a stopper against the distal part of the central tube 101 when the telescopic tube is axially pushed into central tube 101.

The distal part 116 of the catheter is threaded onto body 109 so that its proximal part rests against sleeve 118 and the distal part of intermediate tube 103 at the same time as the proximal part of the intermediate tube 103 without force rests against ring 105 which in turn 30 rests against stop ring 104. In this position telescopic tube 102 can be axially displaced forwardly or rearwardly in central tube 101.

A positioning balloon 130 and treatment balloon 131 are shown in FIG. 3, and the distal part 132 of the treatment balloon 131,as well as the positioning, balloon 130 are attached to sleeve 118. The proximal part of treatment balloon 131 is attached to the central tube 101 (not shown in the Figures).

The axial length of the treatment balloon 131 can be adjusted before treatment by displacing telescopic tube 102 in relation to central tube 101 until the distance between the proximal attachment of the treatment balloon 131 onto central tube 101 and the distal attachment to telescopic tube 132 corresponds to the desired length. Locking of this position takes place by rotating the distal part 116 to engage the intermediate tube 103 against locking ring 105 so as to result in expansion thereof.

FIG. 8 also shows a flexible capillary tube 133 through which air can be injected to expand the positioning balloon 130. By designing the distal part of the capillary tube 133 as a coil the capillary tube can move along with extension or shortening of the telescopic arrangement.

The alternative arrangement for providing adjustability of the axial length of the treatment balloon as shown in FIGS. 8 and 9 gives an added advantage in relation to the design according to FIG. 1. By moving the system for adjustment of axial length of the treatment balloon from the intermediate or handle part of the catheter to the distal part thereof greater freedom will be obtained in regard to the design of the intermediate, part of the catheter. Accordingly this part can be made flexible or can be given a bent shape for better accommodation to a particular treatment site, such as the prostate.

It is to be noted that many variations of the invention as described are conceivable and within the skill of the artisan and the invention is to be limited solely by the scope of the appended claims.

The invention claimed is:

1. Balloon catheter for exerting internal pressure on surrounding tissue of a mammalian duct or cavity in a section thereof having a substantially circular cylindrical configuration comprising:
    an elongate, rigid distal section and a flexible and elastic balloon accommodating said distal section which, together with said balloon is intended for insertion into said duct or cavity section,
    means for the supply of a pressure medium for the expansion of said balloon,
    an intermediate section and a proximal section for operating the device wherein said distal and intermediate sections contain a central tube, a distal part of the central tube is provided with at least one outlet for said medium within said balloon, and an intermediate part of the central tube is surrounded by an axially displaceable tube, a distal end of the displaceable tube has the proximal end of said balloon attached, and said balloon has an envelope which is constituted by at least one substantially gas- and liquid-impermeable and elastic internal layer and a restricting layer of limited radial expansion, said expansion being substantially independent of the axial length of said balloon, and
    means for axially interlocking said central and axially displaceable tubes to each other in a position corresponding to a desired length of said balloon.

2. Balloon catheter according to claim 1, wherein said restricting layer is constituted by one of a braid structure and a spiral structure, and a knitted structure, each structure including filaments of limited elasticity, optionally containing an extra interwoven filament in spiral configuration and of limited elasticity.

3. Balloon catheter according to claim 2, wherein the layer of limited radial expansion is attached to at least one flanking layer.

4. Balloon catheter according to claim 1, wherein said envelope is constituted by a triple-layered structure, where two substantially gas- and liquid-impermeable elastic layers are flanking or embracing a restricting layer of limited radial expansion.

5. Balloon catheter according to claim 4, wherein said layer of limited radial expansion is constituted by a braid structure, the filaments of which have a limited stretchability of about 150 to about 400%.

6. Balloon catheter according to claim 5, wherein the number of filaments is at least about 20 in each direction of winding.

7. Balloon catheter according to claim 6, wherein crossing filaments define an axially directed angle α lying within the range about 100° to about 140°.

8. Balloon catheter according to claim 5, wherein crossing filaments define an axially directed angle α lying within the range about 100° to about 140°.

9. Balloon catheter according to claim 4, wherein the layer of limited radial expansion is attached to at least one flanking layer.

10. Balloon catheter according to claim 1, wherein, as an alternative, said layers are integrated so as to constitute one single layer.

11. Balloon catheter according to claim 1, wherein the layer of limited radial expansion is attached to at least one flanking layer.

12. Balloon catheter according to claim 1, wherein said central tube is composed of at least two telescopic and concentric partially overlapping tubes, one of which protrudes distally and carries the distal end of the balloon, and the other one of which carries the proximal end of the balloon whereby axial relative displacement of said tubes enables balloon length adjustment.

13. Balloon catheter according to claim 1 for treatment of the prostate comprising a positioning balloon attached at the front end of said distal section and being expansible within the urinary bladder by introduction therein of said pressure medium or a separate pressure medium.

14. Balloon catheter according to claim 1, comprising means generating circulation of said pressure medium within or through said balloon.

15. Balloon catheter according to claim 14, comprising a microwave antenna or radio-frequency emitter placed within said distal section, said antenna or emitter creating heat in the interior of surrounding tissue, whereas the circulation pressure medium cools a surface layer of said tissue around the balloon.

16. Balloon catheter according to claim 1 comprising a heating means for heating said pressure medium.

17. Balloon catheter according to claim 16, wherein said heating means is positioned within said balloon.

18. Balloon catheter according to claim 16, wherein said heating means is positioned within said intermediate section.

19. Balloon catheter according to claim 1, comprising a radially expansible stent encompassing said balloon, said stent being deformable to expand synchronously with the radial expansion of the balloon when inserted in said duct or cavity, thereby being retained expanded therein upon withdrawal of the catheter from said duct or cavity.

20. Balloon catheter according to claim 19, wherein said stent is made of a thermoplastic material.

21. Balloon catheter according to claim 20, wherein said material is biodegradable, such as selected from PCA, PLLA and PLGA.

22. Balloon catheter according to claim 21, wherein said stent has been made subject to heat forming at a temperature near melting temperature to give a desired stent configuration as implanted, and then cold formed to a desired configuration for insertion.

23. Balloon catheter according to claim 19, wherein said stent has been made subject to heat forming at a temperature near melting temperature to give a desired stent configuration as implanted, and then cold formed to a desired configuration for insertion.

24. Balloon catheter according to claim 23, wherein said stent has been made subject to heat forming at a temperature near melting temperature to give a desired stent configuration as implanted, and then cold formed to a desired configuration for insertion.

25. Balloon catheter according to claim 19, comprising means for partially deflating the balloon after expansion thereof for maintaining a desired diameter of the stent as implanted.

26. A method of treatment of a mammalian duct or cavity in a section thereof having a substantially circular cylindrical configuration by exerting an internal pressure on surrounding tissue thereof, comprising the steps:
   a) estimating the axial extension of said section;
   b) adjusting and securing to each other a central tube and an outer axially displaceable tube with one end of an elastic balloon attached such that a distance between axial ends of the elastic balloon match said axial extension;
   c) inserting the balloon thus prepared into said duct or cavity section;
   d) initiating treatment by expanding said balloon by introducing a pressurized fluid therein to exert pressure on said walls to widen to a predetermined degree said duct or cavity within said section by using a balloon of predetermined limited radial expansion;
   e) deflating said balloon and withdrawing same from said duct or cavity section.

27. A method according to claim 26, characterized by the further steps:
   f) applying onto said balloon before renewed insertion thereof a radially expansible stent capable of radial deformation;
   g) inserting said balloon carrying said stent into said section;
   h) expanding said balloon by introducing a pressurized fluid to expand the stent; and
   i) releasing the pressure to deflate the balloon and withdrawing same leaving the stent behind in an expanded state.

28. A method according to claim 27, wherein step b) is performed one of after step c), and after step d).

29. A method according to claim 27, wherein the pressure treatment is combined with heating to maintain pressure and temperature for a period of time to achieve a therapeutic effect in the tissue to be treated.

30. A method according to claim 26, wherein step b) is performed one of after step c), and after step d).

31. A method according to claim 30, wherein the pressure treatment is combined with heating to maintain pressure and temperature for a period of time to achieve a therapeutic effect in the tissue to be treated.

32. A method according to claim 26, wherein the pressure treatment is combined with heating to maintain pressure and temperature for a period of time to achieve a therapeutic effect in the tissue to be treated.

33. A method according to claim 32, wherein said fluid is circulated within or through said balloon.

34. A method according to claim 33, wherein said fluid also acts as a heating medium.

35. A method according to claim 34, directed to treatment of a prostate, comprising heating to maintain a temperature for a period of time resulting in partial necrosis of prostatic tissue.

36. A method according to claim 33, directed to treatment of a prostate, comprising heating to maintain a temperature for a period of time resulting in partial necrosis of prostatic tissue.

37. A method according to claim 32, wherein heating is provided by the generation of microwaves, the circulating pressure medium acting as coolant of the surface of surrounding tissue adjacent to the balloon.

38. A method according to claim 37, directed to treatment of a prostate, comprising heating to maintain a temperature for a period of time resulting in partial necrosis of prostatic tissue.

39. A method according to claim 32, directed to treatment of a prostate, comprising heating to maintain a temperature for a period of time resulting in partial necrosis of prostatic tissue.

40. A method according to claim 26, wherein the further step of applying onto the balloon before insertion thereof a radially expansible stent which is expanded by deformation synchronously with the expansion of the balloon said stent being left expanded behind upon removal of said catheter.

41. A method according to claim 40, wherein said stent is made of a thermoplastic material, the method comprising the steps:
   a) inserting said balloon carrying said stent into said duct or cavity such as a prostatic urethra;
   b) expanding said balloon by introducing a pressurized fluid and supplying heat sufficient to soften the stent to expand same and to widen said;
   c) maintaining pressure and heating for a period of time and at a temperature resulting in partial necrosis of surrounding tissue;
   d) interrupting heating for lowering temperature to fortify the stent; and
   e) deflating the balloon and withdrawing same while leaving the stent behind in an expanded state.

42. A method according to claim 41, wherein said stent is constituted by a thermoplastic polymer and is made subject to heat forming at a temperature near melting temperature to give a desired stent configuration as implanted, and then cold formed to a desired configuration for insertion, the deflation of the balloon in step e) taking place before or simultaneously with interrupting heating.

43. A method according to claim 42, wherein after step c) the balloon is partially deflated for maintaining a desired diameter of the stent.

44. A method according to claim 41, wherein after step c) the balloon is partially deflated for maintaining a desired diameter of the stent.

* * * * *

UNITED STATES PATENT AND TRADEMARK OFFICE
CERTIFICATE OF CORRECTION

PATENT NO. : 7,156,860 B2  Page 1 of 1
APPLICATION NO. : 10/296127
DATED : January 2, 2007
INVENTOR(S) : Hans I. Wallsten It is certified that error appears in the above-identified patent and that said Letters Patent is hereby corrected as shown below:

On Title Page

Item (30) Foreign Application Priority Data:

"May 26, 2000    (CH) ..............1978/00
February 9, 2001  (CH)...............00404/01" should read Item (30) Foreign Application Priority Data:

--May 26, 2000    (SE) ..............1978/00
February 9, 2001  (SE)...............00404/01--.

Signed and Sealed this

Third Day of April, 2007

JON W. DUDAS
*Director of the United States Patent and Trademark Office*